(12) United States Patent
Werner et al.

(10) Patent No.: US 11,371,495 B2
(45) Date of Patent: Jun. 28, 2022

(54) AIR PUMP WITH RETRACTABLE NEEDLE AND/OR METHOD OF MAKING THE SAME

(71) Applicant: PERFORMANCE CREATIONS LLC, Severna Park, MD (US)

(72) Inventors: Gabriel Werner, Severna Park, MD (US); Nathan Wagener, Severna Park, MD (US)

(73) Assignee: PERFORMANCE CREATIONS LLC, Severna Park, MD (US)

( * ) Notice: Subject to any disclaimer, the term of this patent is extended or adjusted under 35 U.S.C. 154(b) by 933 days.

(21) Appl. No.: 15/666,908

(22) Filed: Aug. 2, 2017

(65) Prior Publication Data

US 2018/0038361 A1 Feb. 8, 2018

Related U.S. Application Data

(60) Provisional application No. 62/369,931, filed on Aug. 2, 2016.

(51) Int. Cl.
*F04B 33/00* (2006.01)
*A61M 5/32* (2006.01)
(Continued)

(52) U.S. Cl.
CPC .......... *F04B 33/005* (2013.01); *A61M 5/322* (2013.01); *F04B 33/00* (2013.01);
(Continued)

(58) Field of Classification Search
CPC .... F04B 33/005; F04B 33/00; F04B 39/0005; F04B 39/10; F04B 39/121; A61M 5/322; A61M 5/3221
See application file for complete search history.

(56) References Cited

U.S. PATENT DOCUMENTS 2,576,687 A 11/1951 Krehbiel
2,615,446 A * 10/1952 Lingenfelter ......... A61M 5/282
604/212

(Continued)

FOREIGN PATENT DOCUMENTS

FR 602 757 3/1926
FR 2 653 341 4/1991
JP 4520864 5/2010

OTHER PUBLICATIONS

Internet Publication on Amazon for a commercially available air pump "Baden 4-Inch Air Pump, Blue".*

(Continued)

*Primary Examiner* — Essama Omgba
*Assistant Examiner* — Dnyanesh G Kasture
(74) *Attorney, Agent, or Firm* — Nixon & Vanderhye PC (57) ABSTRACT

Certain example embodiments relate to an air pump for balls, tires, toys, and/or the like and include a retractable base, which facilitates the storage of the needle(s) and/or other adapter(s) inside of the pump itself. This arrangement reduces the chances that it/they will break because it/they is/are protected inside of the pump and need not be repeatedly attached/detached. The pump in certain example embodiments includes a tube body into which the retractable base retracts, a plunger disk, a guide system including one or more guides for guiding the plunger disk and/or base within the tube body, a locking mechanism to help lock the base in extended and/or retracted positions, and a handle. The pump safely stores at least one needle/adapter in the tube body. In the event that a needle breaks, it may be replaced as if it were a conventional pump.

19 Claims, 5 Drawing Sheets

(51) Int. Cl.
  *F04B 39/00* (2006.01)
  *F04B 39/10* (2006.01)
  *F04B 39/12* (2006.01)
(52) U.S. Cl.
  CPC .......... *F04B 39/0005* (2013.01); *F04B 39/10* (2013.01); *F04B 39/121* (2013.01)

(56) References Cited

U.S. PATENT DOCUMENTS

| | | | | |
|---|---|---|---|---|
| 3,313,215 | A * | 4/1967 | Bieri | B22D 11/126 92/110 |
| 4,736,675 | A | 4/1988 | Stoll | |
| 4,973,316 | A * | 11/1990 | Dysarz | A61M 5/3232 604/110 |
| 5,000,738 | A | 3/1991 | Lavallo et al. | |
| 5,176,643 | A | 1/1993 | Kramer et al. | |
| 5,306,226 | A * | 4/1994 | Salama | A61F 2/0009 128/DIG. 25 |
| 5,515,610 | A * | 5/1996 | Levin | B26B 1/04 30/155 |
| 5,993,419 | A | 11/1999 | Lo et al. | |
| 6,017,201 | A | 1/2000 | Yang | |
| 6,173,928 | B1 | 1/2001 | Coats | |
| 6,422,832 | B1 | 7/2002 | Wang | |
| 6,458,597 | B1 * | 10/2002 | Andrien, Jr. | H01J 49/0445 250/281 |
| 6,736,619 | B2 | 5/2004 | Wu | |
| 7,278,986 | B1 * | 10/2007 | Frost | A61M 5/3232 604/195 |
| 7,445,533 | B2 | 11/2008 | Norton et al. | |
| 8,522,665 | B2 * | 9/2013 | Holt | F04B 33/005 92/58.1 |
| 2003/0187401 | A1 * | 10/2003 | Doyle | A61M 5/3243 604/198 |
| 2007/0060886 | A1 * | 3/2007 | Knepshield | A61M 5/322 604/110 |
| 2009/0242471 | A1 * | 10/2009 | Shinoda | B01D 61/025 210/170.11 |
| 2010/0185147 | A1 * | 7/2010 | Chen | A61M 5/322 604/110 |
| 2012/0073161 | A1 * | 3/2012 | Doyle | A43B 13/203 36/29 |
| 2012/0226239 | A1 * | 9/2012 | Green | A61M 5/1782 604/192 |
| 2016/0144676 | A1 | 5/2016 | Neir et al. | |
| 2017/0239425 | A1 * | 8/2017 | Castanon | A61M 5/3234 |

OTHER PUBLICATIONS

International Preliminary Report on Patentability dated Feb. 5, 2019, 7 pages.
Indiegogo, Aer—Automatic Ball Pump, retrieved Jul. 31, 2017, 1 page. https://www.indiegogo.com/projects/aer-the-ultimate-precision-ball-pump-sports#/.
Search Report and Written Opinion dated Oct. 13, 2017 in corresponding PCT Application No. PCT/US2017/045041, 14 pages.

* cited by examiner

AIR PUMP WITH RETRACTABLE NEEDLE AND/OR METHOD OF MAKING THE SAME

CROSS-REFERENCE TO RELATED APPLICATION

This application claims the benefit of U.S. Application Ser. No. 62/369,931 filed on Aug. 2, 2016, the entire contents of each of which are hereby incorporated herein by reference.

TECHNICAL FIELD

Certain example embodiments described herein relate to pumps for inflating objects. More particularly, certain example embodiments described herein relate to air pumps with needles that are retractable into the bodies thereof.

BACKGROUND AND SUMMARY

Pumps are used to inflate a variety of different inflatable objects including, for example, hand- and foot-operated pumps for inflating sports balls, vehicle tires (including bicycle and automobile tires, for example), toys, etc. Although some pumps are designed for use in a specific location (such as, for example, in a home garage, basement, mechanic's shop, or the like), other pumps are intended to be transported so that they can be used practically anywhere. See, for example, U.S. Pat. Nos. 8,522,665; 6,736,619; 6,422,832; 6,173,928; and 6,017,201, the entire contents of which are hereby incorporated herein by reference.

Typically, a pump will use some type of adapter to connect its pump nozzle to the object to be inflated. Many pumps use slender needle-type adapters that are inserted into a valve on the object to be inflated to form a secure, basically air-tight fit with the object to be inflated for efficient pumping. Many of these pumps are provided with different needles of varying sizes so that the pump can be used with a number of different types of objects with different valve sizes.

Although needle-type connects are very widely used, they are susceptible to being damaged when stored and/or moved. Indeed, slender needles typically will extend straight outwardly from their pumps' heads, so such needles are not protected from damage by any part of the pump. Because of the slender shape of such needles, the needles may be prone to being bent, deformed, broken off, or otherwise damaged, when stored and/or moved. For example, an athlete, coach, team manager, parent/guardian, or other person, may transport and store a hand pump for a sports ball in a gym bag. The pump may not be secured within the bag, allowing the pump to move or bounce around, potentially damaging the needle and/or the location on the pump where the needle is attached. In addition, or in the alternative, other items may be transported within the bag and may damage the needle or the pump as a result of their striking against or otherwise coming into contact with the pump and needle.

To reduce the likelihood of damage being done to needles, owners often simply remove them from their pumps. However, because there oftentimes is no easy way to store needles, they unfortunately are easily lost and need to be replaced. Furthermore, needles also can be easily damaged when screwed into and out from a ball pump. Thus, repeated attachment/detachment of a needle can increase the likelihood of its being damaged in some way.

Certain example embodiments address these and/or other concerns. For instance, certain example embodiments relate to an air pump for balls, tires, toys, and/or the like and include a retractable base, which facilitates the storage of the needle(s) and/or other adapter(s) inside of the pump itself. This arrangement allows for the guaranteed storage of the needle(s) and/or other adapter(s), and reduces the chances that it/they will break because it/they is/are protected inside of the pump and need not be repeatedly attached/detached. In addition to the retractable base, the pump in certain example embodiments includes a tube body into which the retractable base retracts, a plunger disk, a guide system including one or more guides for guiding the plunger disk and/or base within the tube body, a locking mechanism to help lock the base in extended and/or retracted positions, and a handle. The pump safely stores at least one needle/adapter in the tube body. In the event that a needle breaks, it may be replaced as if it were a conventional pump (e.g., by being unscrewed and having a replacement newly screwed in, or via other detachment/attachment means).

In certain example embodiments, a pump is provided. The pump includes an elongate body, and a base is located within the body. A needle is connected to the base. A plunger is located within the body and movable therein to compress ambient air to increase pressure of the air within the body of the pump and force the air through the needle and into an inflatable object. A guide along which the plunger and base are arranged to travel is provided, as is a locking mechanism. The base is movable between extended and retracted positions as desired, with the extended and retracted positions being disposed along a common axis corresponding to directions of travel facilitated by the guide. The needle extends outwardly from an end of the body when the base is in the extended position, and the needle is stowed within the body when the base is in the retracted position. The locking mechanism is configured to engage and lock the base in the extended position when the base is moved to the extended position, and to restrict movement in the opposite direction until disengaged.

In certain example embodiments, a portable, handheld pump is provided. The pump includes a body. A base is movable within the body, and the base includes an aperture. A plunger is located within the body and movable therein to force ambient air through the aperture and into an inflatable object. The base is movable between extended and retracted positions as desired. A locking mechanism is configured to engage and lock the base in the extended position when the base is moved to the extended position, and to restrict movement in the opposite direction until disengaged.

In certain example embodiments, a method of making a handheld pump is provided. The method includes: providing a body of the pump; locating a movable base within the body, the base including an aperture; locating a plunger within the body; and orienting the plunger and base relative to the body of the pump so that the plunger and base can travel therealong. The plunger is movable within the body to force ambient air through the aperture and into an inflatable object. The base is movable between extended and retracted positions as desired. A locking mechanism is configured to engage and lock the base in the extended position when the base is moved to the extended position, and to restrict movement in the opposite direction until disengaged.

The features, aspects, advantages, and example embodiments may be used separately and/or applied in various combinations to achieve yet further embodiments of this invention.

BRIEF DESCRIPTION OF THE DRAWINGS

These and other features and advantages may be better and more completely understood by reference to the following detailed description of exemplary illustrative embodiments in conjunction with the drawings, of which.

DETAILED DESCRIPTION

Certain example embodiments relate to an air pump for balls, tires, toys, and/or the like and include a retractable base, which facilitates the storage of the needle(s) and/or other adapter(s) inside of the pump itself. The pump in certain example embodiments includes a tube body into which the retractable base retracts, a plunger disk, a guide system including one or more guides for guiding the plunger disk and/or base within the tube body, a locking mechanism to help lock the base in extended and/or retracted positions, and a handle. The pump safely stores at least one needle/adapter in the tube body. This arrangement advantageously allows for the guaranteed storage of the needle(s) and/or other adapter(s), and correspondingly reduces the chances that it/they will break because it/they is/are protected inside of the pump and need not be repeatedly attached/detached. In the event that a needle breaks, advantageously, it may be replaced as if it were a conventional pump (e.g., by being unscrewed and having a replacement newly screwed in, or via other detachment/attachment means).

Figure 1:
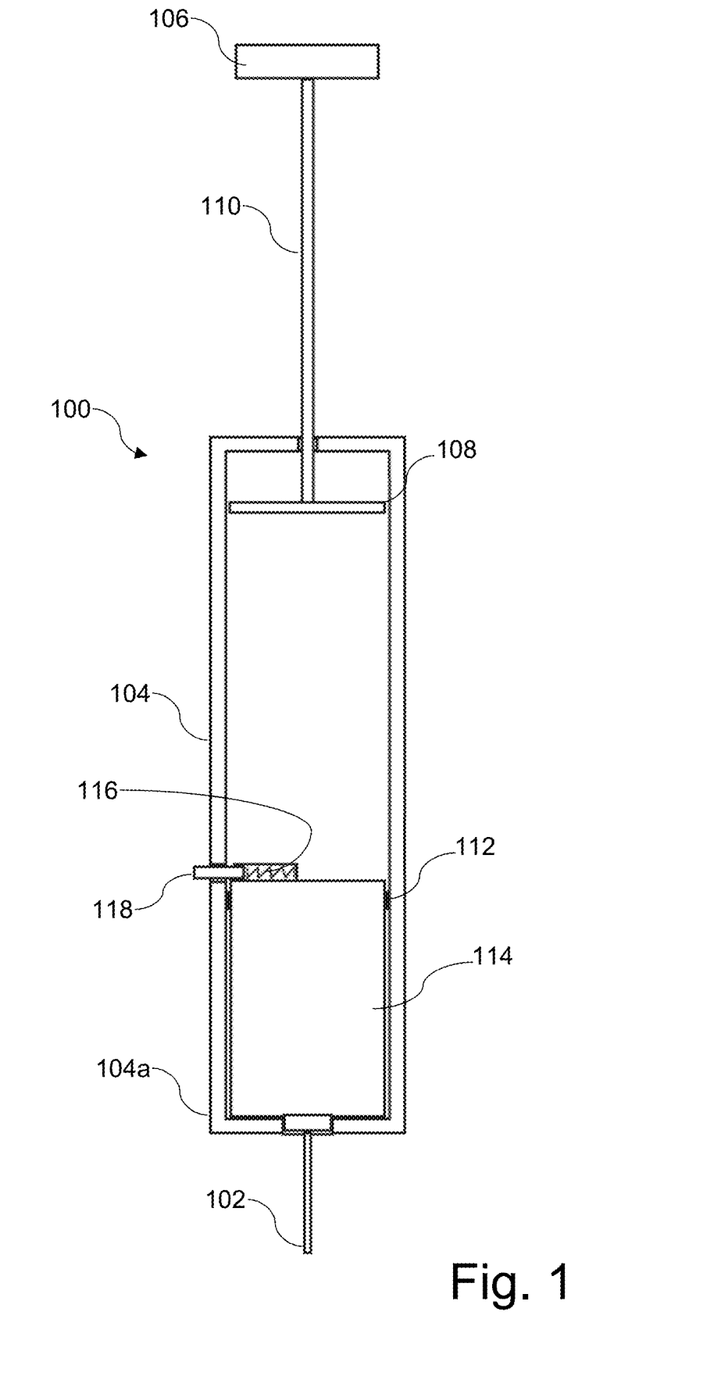
FIG. 1 is a cross-sectional view of an air pump with a retractable needle shown in its extended position, in accordance with a first example embodiment.
Figure 2:
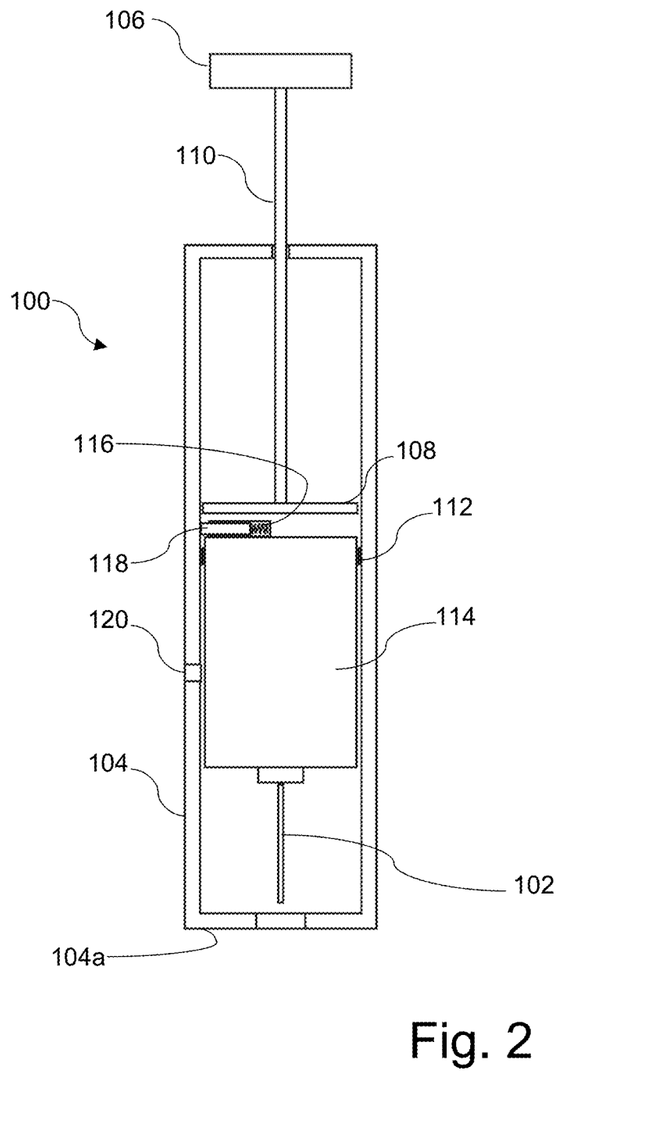
FIG. 2 is a cross-sectional view of the FIG. 1 example embodiment, with the retractable needle shown in its retracted position.

Referring now particularly to the drawings, FIG. 1 is a cross-sectional view of an air pump 100 with a retractable needle 102 shown in an extended position, in accordance with a first example embodiment. FIG. 2 is a cross-sectional view of the FIG. 1 example embodiment, with the retractable needle 102 shown in its retracted position.

In FIG. 1, the retractable needle 102 is in an extended position such that it protrudes from a bottom end (or head) 104a of the tube body 104 of the pump 100 and can be inserted into a ball to inflate it. The handle 106 is at the end of the pump 100 opposite the needle 102 and is attached to a plunger disk 108 via the elongate neck 110. The plunger disk 108 is located in an interior of the tube body 104, roughly through the center of the pump 100. The plunger disk 108 is movable within the tube body 104 to force air through an outlet in the needle 102 in inflating a ball or other object. A guide system (described in greater detail below) facilitates the travel of the plunger disk 108 in the tube body 104, in certain example embodiments. A plunger disk assembly may include the plunger disk 108 and be surrounded by an O-ring. Alternatively, or in addition, an O-ring 112 may be provided around a movable base 114 to which the needle 102 is attached, e.g., helping to form a seal for the internal piston system. An O-ring alternatively or additionally may be provided at the bottom 104a of the tube body 104, proximate to where the needle 102 or other adapter(s) protrudes from the tube body, e.g., forming a seal when the pump 100 is in use to pump air. Although O-rings have been described, it will be appreciated that any suitable seal structure may be used in different embodiments in these and/or other locations.

Operation of the pump is fairly straightforward in terms of its piston action. See, for example, U.S. Pat. Nos. 8,522,665; 6,736,619; 6,422,832; 6,173,928; and 6,017,201, the entire contents of which are hereby incorporated herein by reference. The plunger disk 108 forms a part of the mechanism for compressing ambient air. When the handle 106 is depressed, the plunger disk 108 compresses the air and increases the pressure of the air within the tube body 104, e.g., to begin the flow of air from the pump 100 to an object to be inflated. A one-way valve, such as a poppet valve or the like, may be used to control the direction of air flow, as it typically is desirable to cause air to flow from tube body 104 (acting as a piston chamber) to the needle 102. When the one-way valve is open, air will flow between the tube body 104 (acting as a piston chamber) to the needle 102. The one-way valve may be set to open only when the pressure within the tube body 104 (acting as a piston chamber) reaches or exceeds a predetermined pressure.

Figure 3:
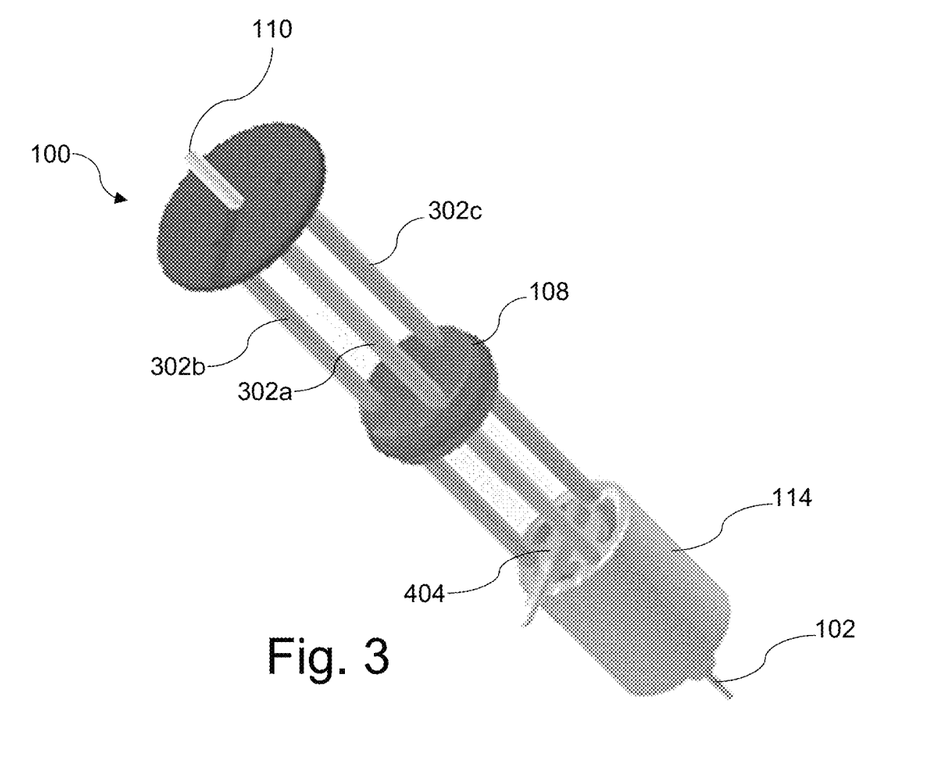
FIG. 3 is a partial perspective view of a portion of the FIG. 1 example embodiment.

FIG. 3 is a partial perspective view of a portion of the FIG. 1 example embodiment, with some components thereof removed to facilitate the following explanation. As shown in FIG. 3, the guide system includes three poles 302a-302c that extent along the length of the pump 100. Although three poles are shown in the FIG. 1 example, it will be appreciated that more or fewer poles may be used in different example embodiments. It also will be appreciated that such poles may be formed from any suitable material such as, for example, metal, plastic, or some other generally rigid material suitable for guiding the plunger disk 108 and/or other components through the tube body 104. Moreover, in certain example embodiments, rails connected to, integral (e.g., extruded, co-extruded, 3D printed, or otherwise formed) with, the tube body 104 may be used in place of, or in addition to, the poles 302a-302c. As will be appreciated from FIGS. 1-2, the poles 302a-302c may float freely within the tube body 104 or connect with an inner surface of the bottom end (or head) 104a of the tube body 104. With respect to the latter, in certain example embodiments, the guide poles 302a-302c or other features may be connected to each of opposite end faces of the body.

Figure 4:
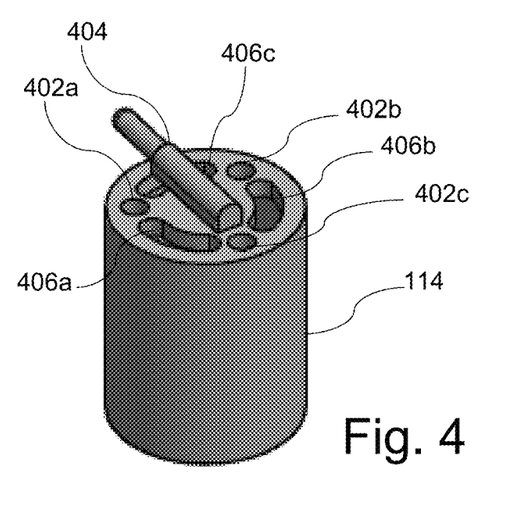
FIG. 4 is an enlarged cross-sectional view of an example base, which may be used in connection with the FIG. 1 example in certain example embodiments.

FIG. 4 is an enlarged cross-sectional view of an example base 114, which may be used in connection with the FIG. 1 example air pump in certain example embodiments. Three holes (e.g., through-holes) 402a-402c accommodate the three pole guides 302a-302c shown and described in connection with FIG. 3. It will be appreciated that more or fewer holes may be provided in order to accommodate more or fewer guide poles or other features, in different example embodiments. Regardless of whether the guide system is implemented to include poles, rails, or other features, the base 114 follows the guide system, and locks into place once the base 114 reaches the bottom of the guide system via a locking system 404. In certain example embodiments, guiding may be provided by enabling the movable base 114 and/or the plunger disk 108 to slide along the inner surface of the tube body 104. That is, the tube body 104 itself may serve to guide these and/or other features between extended and retracted positions. Any suitable locking mechanism may be used.

For example, a biased or spring-loaded button may be affixed to or otherwise travel with the base. In this regard, FIGS. 1-2 show a spring-loaded pin locking system, which includes a spring 116 and a pin or button 118. The spring 116 is compressed when the needle 102 is at least partially retracted into the interior of the tube body 104, causing the pin 118 to be located within interior of the tube body 104 and travel along an inner wall surface thereof. However, when the base 114 is in its extended position, the pin 118 is forced out of the through-hole 120 formed in the tube body 104 via the spring 116 expanding. An O-ring or other seal may be provided around the hole 120 in certain example embodiments.

Thus, in certain example embodiments, the base 114 may be movable between extended and retracted positions as desired, with the extended and retracted positions being disposed along a common axis corresponding to directions of travel facilitated by the guide members. The needle 102 extends outwardly from an end of the tube body 104 when the base 114 is in the extended position, and the needle 102 is stowed within the tube body 104 when the base 114 is in the retracted position. The locking mechanism 404 is configured to engage and lock the base 114 in the extended position when the base 114 is moved to the extended position, and to restrict movement in the opposite direction until disengaged.

When the plunger disk 108 pushes the base 114 while the needle 102 is in an at least partially retracted position, the needle 102 extends from the tube body 104 and the pin or button 118 extends through the hole 120 formed in the tube body 104. The extension of the pin or button 118 through this hole 120 holds the needle 102 in the extended position. The button 118 is depressible, and the base 114 slideable toward the handle 106, in order to allow the needle 102 to retract with modest pressure on the needle 102 and/or base 114. A significant amount of the bottom surface 104a of the tube body 104 may be exposed so that pressure may be provided to the base 114 rather than the needle 102 in certain example embodiments.

In certain example embodiments, a second through-hole may be located closer to the handle 106 and correspond to a locked position. That is, the spring 116 may force the pin 118 through a second hole, located between first hole 120 and an upper portion of the tube body 104 so that the pin 118 is forced through that second hole in order to help maintain the base 114 and the needle 102 in a retracted position within the tube. The pin or button 118 may be depressed, and the plunger disk 108 pushed, in order to cause the base 114 and the needle to travel from this locked, retracted position to the locked extended position.

As indicated above, spring-loaded mechanisms needed not be used to perform locking operations with respect to either or both of the extended and retracted positions. Biased barb members and/or other features may be used in this regard.

Features may be implemented in order to avoid having to depress the base 114 and/or the needle 102 when performing a retracting action, in certain example embodiments. For instance, interlocking, interconnecting, or otherwise complementary features may be provided to the surface of the plunger disk 108 closest the base 114 and to the surface of the base 114 closest the plunger disk 108. For example, complementary hooks or the like may be formed on these two surfaces. When the needle 102 is to be retracted, the hooks or other features may be made to connect with one another, e.g., by rotating the handle 106. The handle 106 may be drawn upwardly while the pin 118 is depressed, thereby obviating the need to provide pressure to the needle 102 and/or base 114. To stow the pump 102, the features may be disengaged and the handle 106 may be depressed far enough to move into the body of the pump 100 but without causing the base 114 to move down. The features also may be disengaged before, during, or after the base 114 is moved to its extended position.

Alternatively, or in addition, once the locking mechanism is released while the needle 102 is in its extended position, springs or other mechanisms may provide a biased force such that the base 114 "automatically" recesses at least partially into the tube body 104, thereby reducing the amount of pressure required with respect to the base 114 and/or needle 102. In other words, in certain example embodiments, the base 114 may have a biased force applied thereto such that the base 114 is biased to move towards the retracted position when the lock of the locking mechanism 404 is disengaged. The base may ride on a track or the like to facilitate this and/or other movable action.

Referring once again to FIG. 4, one or more elongate openings or recesses may be formed in the base 114. Three such openings 406a-406c are shown by way of example and without limitation in the FIG. 4 embodiment. It will be appreciated that more or few of these and/or other shapes (e.g., rectangular, circular, ellipsoid, or other) may be used in different example embodiments. These recesses may facilitate the movement of air in the tube body 104 in certain example embodiments. The openings 406a-406c may be through-holes in certain example embodiments, e.g., to allow air to pass through the base 114. The holes 406a-406c may taper in certain example embodiments, e.g., to facilitate compression of the air.

Figure 5:
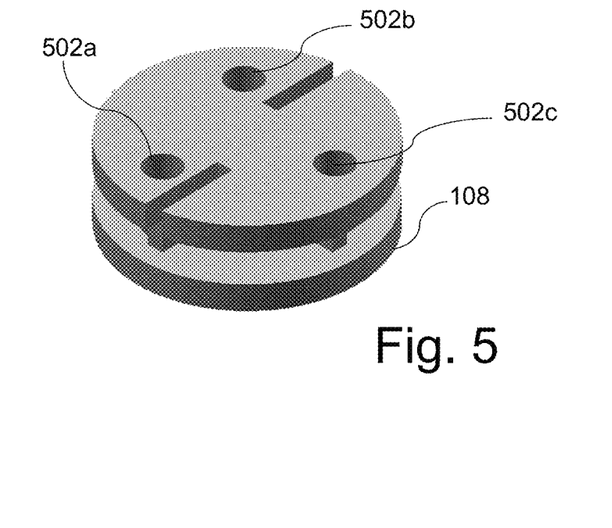
FIG. 5 is an example plunger disk 108, which may be used in connection with the FIG. 1 example air pump.

FIG. 5 is an example plunger disk 108, which may be used in connection with the FIG. 1 example air pump. The plunger disk 108 is attached to the plunger handle 106 in certain example embodiments. As noted above, when the plunger handle 106 is pushed when the needle 102 is in the retracted state, the plunger disk 108 pushes the base 114 down into the locked, extended position. The plunger disk 108 also acts as an air pushing mechanism inside of the pump 100. The holes 402a-402c in the base 114 and the holes 502a-502c in the plunger disk 108 are aligned within the tube body 104 to accommodate the guide poles 302a-302c or other features. Thus, although three holes 502a-502c are shown in the example plunger disk 108 of FIG. 5, more or fewer holes or the like may be provided in different example embodiments. Thus, although different guide systems with different guide members may be used, the plunger disk 108 and the base 114 may each include notches, holes, and/or other features shaped, sized, and arranged, to accommodate such members. As noted elsewhere, guiding may be provided by enabling the plunger disk 108 and/or other structures to travel along an inner surface of the tube body 104. An O-ring or other seal facilitating one-way vacuum and/or air fluid movement may be provided between the upper and lower disk comprising this example plunger disk 108, e.g., with a cross- or otherwise-shaped center section holding it in place relative to the plunger disk 108. It is noted that other plunger disk configurations may be used in different example embodiments. It also is noted that the plunger need not necessarily be disk-shaped in certain example embodiments.

It will be appreciated from the above that certain example embodiments enable a user to use the handle to push the plunger disk to push the base into the extended position. By doing this, the retractable base is pushed down into place along a series of guides, if guides are used, inside the body of the pump. Once the base is in place, the button will move outwardly, locking the base into place so the user can pump, using the handle to move the plunger disk along the length of the tube and force air out through an aperture in the needle and into the object being pumped. Once the user is done pumping, the plunger disk is pulled into the extended position and the button is pushed, allowing for the needle to retract back into the body of the pump, safely storing it for later (re)use.

Although certain example embodiments have been described in connection with a T-shaped handle 106, it will be appreciated that other configurations may be used in different example embodiments. For instance, circular, ovular, rectangular, or other arrangements may be provided for accommodating a user's hand. Finger grips alternatively or additionally may be provided. In certain example embodiments, instead of hand pump plunging action, foot pumps may be provided.

In certain example embodiments, the needle may be connected to a hose. The hose may be retractable within the tube body 104 in certain example embodiments. For instance, it may coil around an interior of the tube body 104 and/or a feature located therein (e.g., a substantially central generally columnar feature separate from any guide members, a thick guide member in the approximate center of the tube body 104, around the periphery of poles such as those shown in FIG. 3, etc.). In certain example embodiments, the hose may be retractable by virtue of being on a spring-loaded attachment. In other example embodiments, a hand crank may be provided to cause the hose to coil around a reel.

Although certain example embodiments have been described in connection with a single needle, it will be appreciated that other reusable adapters for forcing air into an object may be provided in place of, or in addition to, a single needle. For example, a plurality of different adapters may be mounted to an end portion of a base, e.g., on a rotatable attachment. The attachment may be rotated to cause an adapter to be used to align with an opening in the base, so as to force air through the selected adapter.

Figure 6:
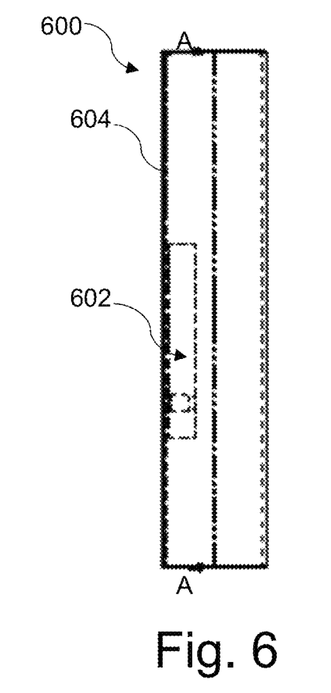
FIG. 6 is a side view of a portion of an air pump with a retractable needle, in accordance with a second example embodiment.
Figure 7:
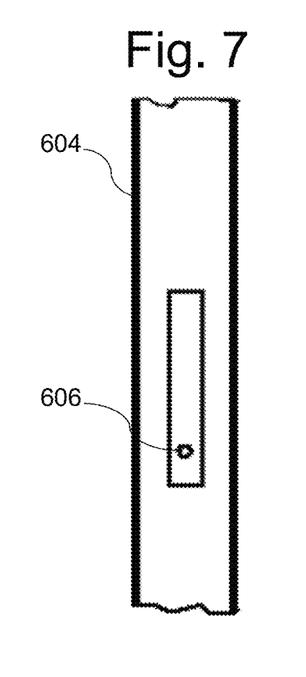
FIG. 7 is a view of the FIG. 6 example air pump along the A-A section line.
Figure 8:
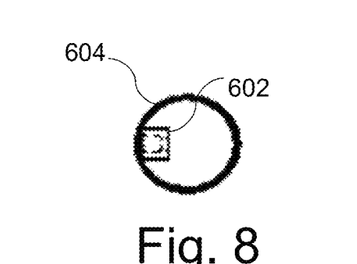
FIG. 8 is a top plan view of the FIG. 6 example air pump.

One alternative arrangement will now be described in connection with FIGS. 6-10. In that regard, FIG. 6 is a side view of a portion of an air pump 600 with a retractable needle in accordance with a second example embodiment, FIG. 7 is a view of the FIG. 6 example air pump 600 along the A-A section line, and FIG. 8 is a top plan view of the FIG. 6 example air pump 600. In this example, rather than guide poles, a rectangular extrusion 602 is formed on the inside of the tube 604. The rectangular extrusion 602 acts as a guide system for a different version of the retractable base (described below in connection with FIGS. 9-10). Similar to the above, the tube 604 has a hole 606 to allow the button on the retractable base to lock into place and maintain the needle in its position, extended outside of the tube 604.

Figure 9:
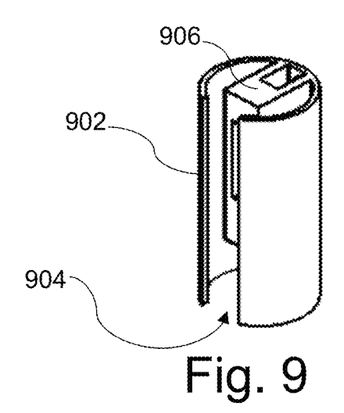
FIG. 9 is a perspective view of an alternative base which may be used in connection with the FIG. 6 example air pump.
Figure 10:
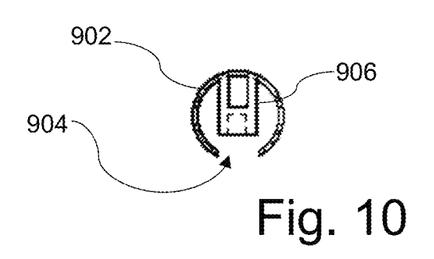
FIG. 10 is a top plan view of the FIG. 9 example base.

FIG. 9 is a perspective view of an alternative base 902 which may be used in connection with the FIG. 6 example air pump 600, and FIG. 10 is a top plan view of the FIG. 9 example base. The retractable base 902 is a cylinder with a cut 904 in it. The cut 904 allows the retractable base 902 to be guided by the extrusion 602 formed on the inner wall of the tube body 604. The retractable base 902 has a rectangular extrusion 906 that stores the button that will extend from the tube 604 to keep the base 902 in the locked, extended position. It will be appreciated that the guide system here or elsewhere may extend along a substantial (e.g., at least 25%, more preferably at least 33%, and possibly 50% or more) portion of the length of the tube.

In certain example embodiments, the pump need not come with an adapter (e.g., a needle or the like). For instance, an adapter may be later screwed onto the pump, e.g., such that it is in fluid communication with an aperture formed in the base or elsewhere, e.g., so that ambient air can be forced into an inflatable object. In certain example embodiments, the adapter may be designed for repeated use without removal.

As alluded to above, methods of making the example pumps described herein also are contemplated. These techniques may include extrusion, co-extrusion, laser printing, and/or the like. By way of example and without limitation unless expressly claimed, a method of making a handheld pump may include: providing a body of the pump; locating a movable base within the body, the base including an aperture; locating a plunger within the body; and orienting the plunger and base along a guide (which may simply be the inner surface of the body of the pump) so that the plunger and base can travel along the guide. The plunger is movable within the body, along the guide, to force ambient air through the aperture and into an inflatable object. The base is movable between extended and retracted positions as desired. A locking mechanism is configured to engage and lock the base in the extended position when the base is moved to the extended position, and to restrict movement in the opposite direction until disengaged. The method may include additional steps, e.g., to provide additional features and/or functionality as disclosed herein.

Although certain example embodiments have been described as including a locking mechanism being provided on the movable base, it will be appreciated that such locking mechanisms may be incorporated into the body of the base in different example embodiments. It also will be appreciated that mechanisms for locking the base in place may be provided elsewhere and that auxiliary locking systems may be provided, e.g., such that one locking mechanism is provided in or on the base while another locking mechanism is located elsewhere.

Although certain example embodiments have been described as relating to a tube and have shown pumps that are generally cylindrical, it will be appreciated that other configurations may be used in different example embodiments.

It will be appreciated that the modification discussed above in connection with the FIG. 1 example embodiment may be applied to other designs as well. For instance, different locking mechanisms, different handle options, locks for extended and retracted states, hose attachment, a multi-adapter heads, and/or the like may be provided in connection with different embodiments of this invention.

It will be appreciated that the air pump described herein may be used to force air into a variety of different articles including, for example, balls used in sporting events (e.g., soccer balls, basketballs, footballs, volleyballs, etc.), tires, toys, and/or the like.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A manually-driven hand-pump, comprising:
an elongate body;
a base located within the body;
a reusable needle connected to the base;
a plunger, located within the body and movable therein to compress ambient air to increase pressure of the air within the body of the hand-pump and force the air through the needle and into multiple inflatable objects;
a guide along which the plunger and base are arranged to travel;
a hole formed in the body; and
a locking mechanism;
wherein the base is repeatably movable between fully extended and fully retracted positions as desired, the fully extended and fully retracted positions being disposed along a common axis corresponding to directions of travel facilitated by the guide, wherein the needle extends outwardly from an end of the body when the base is in the fully extended position, and wherein the needle and base are entirely stowed within the body when the base is in the fully retracted position;
wherein the locking mechanism is configured to engage and lock the base in the fully extended position each of plural times the base is moved to the fully extended position to enable pumping of air, and to restrict movement in the opposite direction until disengaged,
wherein the locking mechanism is disposed on the base and comprises a pin attached to a spring,
wherein the pin is arranged to extend through the hole when the base is moved to the fully extended position, and
wherein the pin is depressible to disengage the locking mechanism and allow for movement of the base.

2. The hand-pump of claim 1, wherein the base is repeatably movable to the fully extended position from intermediate positions along the along the common axis between the fully extended and fully retracted positions in response to the plunger contacting and pushing the base.

3. The hand-pump of claim 1, wherein the base has a biased force applied thereto such that the base is biased to move from the fully extended position towards the fully retracted position when the locking mechanism is disengaged.

4. The hand-pump of claim 1, wherein:
the pin is arranged to extend through the hole when the base is moved to the fully extended position and prohibit the base both from moving further along the common axis beyond the fully extended position and from moving along the common axis towards the fully retracted position, and
the pin is depressible to disengage the locking mechanism and allow the base to move along the common axis towards the fully retracted position.

5. The hand-pump of claim 1, further comprising first and second holes formed in the body, the first and second holes being provided along a length of the elongate body and being remote from one another,
wherein the locking mechanism is further configured to engage and lock the base in the fully retracted position when the base is moved to the fully retracted position, and to restrict movement in the opposite direction until disengaged,
wherein the locking mechanism is disposed on the base and comprises a pin attached to a spring,
wherein the pin is arranged to extend through the first hole when the base is moved to the fully extended position,
wherein the pin is arranged to extend through the second hole when the base is moved to the fully retracted position, and
wherein the pin is depressible to disengage the locking mechanism.

6. A manually-driven hand-pump, comprising:
an elongate body;
a base located within the body;
a reusable needle connected to the base;
a plunger, located within the body and movable therein to compress ambient air to increase pressure of the air within the body of the hand-pump and force the air through the needle and into multiple inflatable objects;
a guide along which the plunger and base are arranged to travel; and
a locking mechanism;
wherein the base is repeatably movable between extended and retracted positions as desired, the extended and retracted positions being disposed along a common axis corresponding to directions of travel facilitated by the guide, wherein the needle extends outwardly from an end of the body when the base is in the extended position, and wherein the needle and base are entirely stowed within the body when the base is in the retracted position; and
wherein the locking mechanism is configured to engage and lock the base in the extended position each of plural times the base is moved to the extended position to enable pumping of air, and to restrict movement in the opposite direction until disengaged,
wherein the guide comprises a plurality of guide poles extending along a length of the elongate body, and
wherein the plunger and the base include holes through which the guide poles are provided.

7. The hand-pump of claim 6, wherein the guide poles are connected to each of opposite end faces of the body.

8. A manually-driven hand-pump, comprising:
an elongate body;
a base located within the body;
a reusable needle connected to the base;
a plunger, located within the body and movable therein to compress ambient air to increase pressure of the air within the body of the hand-pump and force the air through the needle and into multiple inflatable objects;
a guide along which the plunger and base are arranged to travel; and
a locking mechanism;
wherein the base is repeatably movable between extended and retracted positions as desired, the extended and retracted positions being disposed along a common axis corresponding to directions of travel facilitated by the guide, wherein the needle extends outwardly from an end of the body when the base is in the extended position, and wherein the needle and base are entirely stowed within the body when the base is in the retracted position; and
wherein the locking mechanism is configured to engage and lock the base in the extended position each of plural times the base is moved to the extended position to enable pumping of air, and to restrict movement in the opposite direction until disengaged, and
wherein the guide comprises a member on the elongate body along a substantial length thereof.

9. The hand-pump of claim 8, wherein the plunger and the base each include notches shaped, sized, and arranged, to accommodate the member.

10. The hand-pump of claim 9, wherein the member is substantially square in cross section.

11. A portable, handheld pump, comprising:
a body;
a base movable within the body, the base including an aperture;
a first hole formed in the body; and
a plunger located within the body and movable therein to force ambient air through the aperture and into an inflatable object;
wherein the base is repeatably movable between fully extended and fully retracted positions as desired, and
wherein a locking mechanism is configured to engage and lock the base in the fully extended position when the base is moved to the fully extended position, and to restrict movement in the opposite direction until disengaged,
wherein the locking mechanism is disposed on the base and comprises a pin attached to a spring,
wherein the pin is arranged to extend through the first hole when the base is moved to the fully extended position, and
wherein the pin is depressible to disengage the locking mechanism and allow for movement of the base;
the pump further comprising an adapter in fluid communication with the aperture, the adapter protruding from an end of the pump when the base is locked in the fully extended position and being housable within the pump when the base is fully retracted,
wherein the adapter is designed for repeated use without removal.

12. The pump of claim 11, further comprising a guide along which the plunger and base are arranged to travel,
wherein the guide includes one or more generally elongate guide features located within the body, the base and the plunger being sized, shaped, and arranged to accommodate the one or more generally elongate guide features to facilitate the travel of the base and the plunger within the body.

13. The pump of claim 11, wherein the base is movable to the fully extended position in response to the plunger pushing the base.

14. The pump of claim 11, further comprising a second hole formed in the body, the first and second holes being provided along a length of the body,
wherein the locking mechanism is further configured to engage and lock the base in the fully retracted position when the base is moved to the fully retracted position, and to restrict movement in the opposite direction until disengaged, and
wherein the pin is arranged to extend through the second hole when the base is moved to the fully retracted position.

15. The pump of claim 11, wherein the adapter is a needle.

16. The pump of claim 11, wherein the plunger is configured to be manually driven.

17. The pump of claim 11, being a ball and tire pump.

18. The pump of claim 17, further comprising a further adapter, the adapter and the further adapter each being removably connectable to the base and having different respective types, the adapter being a reusable ball inflation needle and the further adapter being reusable and sized and shaped to inflate tires.

19. A method of making a handheld pump, the method comprising:
providing a body of the pump, the body including a hole;
locating a movable base within the body, the base including an aperture;
locating a plunger within the body; and
orienting the plunger and base relative to the body of the pump so that the plunger and base can travel thereal­ong;
wherein the plunger is movable within the body to force ambient air through the aperture and into inflatable objects,
wherein the handheld pump is assembled so as to permit the base to be repeatably movable between fully extended and fully retracted positions as desired, and
wherein a locking mechanism is configured to engage and lock the base in the fully extended position each of plural times the base is moved to the fully extended position, and to restrict movement in the opposite direction until disengaged, to facilitate pumping of air into inflatable objects when the base is extended to and locked in the fully extended position,
the base including a surface configured to support a reusable adapter usable to inflate the inflatable objects, the base and the adapter being fully retractable into the body of the pump each of the plural times the base is moved to the fully retracted position, at least a portion of the adapter being extendable outwardly from an end of the body of the pump each of plural times the base is moved to the fully extended position,
wherein the locking mechanism is disposed on the base and comprises a pin attached to a spring,
wherein the pin is arranged to extend through the hole when the base is moved to the fully extended position, and
wherein the pin is depressible to disengage the locking mechanism and allow for movement of the base.

* * * * *